US00PP11149P

United States Patent [19]

Wuhl

[11] Patent Number: Plant 11,149

[45] Date of Patent: Dec. 7, 1999

[54] PLUM TREE NAMED 'SIR GEORGE'

[76] Inventor: Eric Wuhl, 5480 E. La., Fresno, Calif. 93727

[21] Appl. No.: 09/064,796

[22] Filed: Apr. 22, 1998

[51] Int. Cl.[6] ..... A01H 5/00

[52] U.S. Cl. ..... Plt./184

[58] Field of Search ..... Plt./184, 185

[56] References Cited

U.S. PATENT DOCUMENTS

P.P. 6,153 4/1988 Chamberlin, Sr. ..... Plt./184

P.P. 6,991 8/1989 Chamberlin, Sr. ..... Plt./184

*Primary Examiner*—Howard J. Locker
*Assistant Examiner*—Wendy A Baker
*Attorney, Agent, or Firm*—Wells, St. John, Roberts, Gregory & Matkin, P.S.

[57] ABSTRACT

A new and distinct variety of plum tree which has been denominated varietally as 'Sir George' which is distinguished by producing uniformly large fruit of a semi-globular form, which has a distinct flavor and which is mature for harvesting and shipment approximately the fourth week of July.

1 Drawing Sheet

BACKGROUND OF NEW VARIETY

The present invention relates to a new and novel variety of plum tree (*Prunus salicina*), which will hereinafter be denominated varietally as the 'Sir George' plum tree, and more particularly to a plum tree which produces a firm, uniformly large fruit having a distinct flavor, and which is mature for commercially harvesting and shipment approximately the last week of July under the ecological conditions prevailing in the San Joaquin Valley of Central California.

The commercial appeal of a given variety of tree fruit may be based upon one or more attributes. Characteristically, commercially successful tree fruit possess noteworthy attributes in several significant categories: flavor, keeping quality, size, shape and skin coloration. The relative importance of these categories are readily evident. However, in reality, the very nature of the evaluation in several key areas renders an overall evaluation of a selected variety, in most cases, somewhat subjective to some degree. Thus, for example, the appeal of the flavor of a given tree fruit may largely be dependent upon personal preferences.

As a consequence, distinctive attributes in the more objective categories such as size, shape and skin coloration are often very important to the commercial success of tree fruit. In this regard, typically the larger the size of the fruit, the greater the commercial appeal. The same may be said of tree fruit having a uniformly distinctive shape and an intense skin coloration. As a general matter, it is unusual to find a variety of tree fruit possessing exemplary attributes in a number of these more objective categories.

ORIGIN AND ASEXUAL REPRODUCTION OF THE NEW VARIETY

The present variety of the plum 'Sir George' was discovered by the inventor in 1989. This new variety was discovered within the cultivated area of his orchard, which is located near Fowler, Calif. The new variety was selected from 112 seedlings found in his orchard, and which was originally planted with the varieties 'Challenger' (unpatented) and 'Showtime', U.S. Plant Pat. No. 8,037. An examination of this new variety reveals that this tree expresses some of the traits of each of these two trees ('Challenger' and 'Showtime') and has some expressions which are intermediate other traits of both trees. Consequently, it is believed that this tree is probably an F1 hybrid of the varieties 'Challenger' and 'Showtime'. The new variety was asexually reproduced at the inventor's direction in June, 1994 by budding the new variety onto 'Nemaguard' rootstock which was growing along Springfield Avenue in Fresno County, Calif. in June of the same year. The resulting asexually reproduced trees were later planted in an orchard located on the inventor's property in Fowler, Calif. These trees have been observed by the inventor since that time and it has been confirmed that the distinctive characteristics of the original tree were expressed in the asexually reproduced trees.

BRIEF DESCRIPTION OF THE DRAWING

The drawing is a color photograph showing four mature fruit of the new variety of plum tree including a first one shown in a top view; a second one shown in side view displaying the suture thereof; a third one showing the shape of the apex of the fruit; a fourth one showing a section of the fruit cut generally along the suture and laid open to display the stone well; a fifth view showing the stone itself; and a portion of the foliage attached to a young terminal twig with several detached leaves showing both the dorsal and ventral coloration thereof.

DETAILED DESCRIPTION

Referring more specifically to the pomological details of this new and distinct variety of plum tree, the following has been observed under the ecological conditions prevailing in the designated orchard near the town of Fowler in Fresno County, Calif. All of the color code designations are by reference to the Maerz & Paul *"Dictionary of Color"*, First Edition, 1930, except where common descriptive color terminology is employed.

TREE

Size: Medium as compared to other varieties.
Figure: Upright and slightly spreading.
Productivity: Productive.
Chilling requirement: Appears to be average when compared to other plums currently growing in the San Joaquin Valley of Central California.
Regularity of bearing: Regular.
Trunk: Medium in size.
Trunk surface texture — Medium to slightly rough.

Trunk color: C-1, Plate 55.
Lenticels:
*Numbers.*—Moderate.
*Size.*—Medium to small when compared to other plum varieties.
Branches:
*Size.*—Medium.
*Surface texture.*—Mature branches appear slightly rough and immature branches appear smooth.
*Color — (one year or older wood).*—Burgundy, E-9, Plate 56.
*Color —(immature wood).*—Spanish Raisin, L-3, Plate 48.
*Lenticels — Numbers.*—Many; Size — small.
*Vigor.*—Terminal growth was 1.8 m in the first year following grafting and totaled 2.7 m by the end of the second year; however this can vary depending upon pruning, training, cultural conditions and rootstock used.

LEAVES

Size:
*Generally.*—Average as compared to other plum cultivars.
*Average length.*—Approximately 89–92 mm. (3.50–3.62 inches).
*Average width.*—Approximately 27–34 mm. (1.06–1.34 inches).
Shape:
*Generally.*—Lanceolate.
Leaf color:
*Upwardly disposed surface.*—Mt. Vernon Green, J-8, Plate 23.
*Downwardly disposed surface.*—Peridot, L-6, Plate 22.
Marginal form: Serrated.
Leaf vein color: Parrot Green, L-6, Plate 21.
Leaf thickness: Approximately 2 mm. (0.8 inch).
Leaf glandular characteristics: Generally considered globular.
Leaf petiole size: Medium.
Leaf petiole length: Approximately 12–15 mm. (0.47–0.59 inches).
Leaf petiole thickness: Approximately 1–2 mm. (0.05–0.08 inches).
Leaf petiole color: Parrot Green, L-6, Plate 21.
Stem glands:
*Form.*—Globose and considered small.
*Position.*—On both sides and at the base of leaf.
*Pattern.*—Alternate.
*Color.*—Green. This color is not particularly distinctive, however.
Stipules: None are evident.

FLOWERS

Flower buds:
*Size.*—Small as compared to other varieties.
*Surface texture.*—Glabrous.
Flowers:
*Date of first bloom.*—February 22nd–24th under the ecological conditions prevailing in the San Joaquin Valley of Central California.
*Size.*—Small (15–17 mm diameter). Non-aromatic.
Petal color: White.
Pistils: One.
Stamens: Approximately 15–20.

Petals: Five.
Fertility: Semi self-fertile.

FRUIT

Maturity when described: Ripe for commercial harvesting and shipment, approximately the fourth week of July in the San Joaquin Valley of Central California.
Size: Generally uniform.
Diameter as measured in the Axial Plane: Approximately 65–67 mm. (2.56–2.65 inches).
Diameter as measured from a location transverse to the suture plane: Approximately 61–67 mm. (2.40–2.64 inches).
Diameter as measured transverse to, and at right angles to the suture plane: Approximately 60–61 mm. (2.36–2.40 inches).
Form: Uniform.
Suture length: Approximately 90–92 mm. (3.35–3.62 inches).
Suture position: Slightly conspicuous and considered shallow.
Ventral surface: Considered smooth.
Stem cavity:
*Width.*—Approximately 18 mm. (0.71 inches).
*Depth.*—Approximately 10 mm. (0.39 inches).
*Length.*—Approximately 20–23 mm. (0.79–91 inches).
Stem cavity shape: Oval.
Stem length: Approximately 14–16 mm. (0.55–0.63 inches).
Stem caliper: Approximately 2 mm. (0.08 inch).
Apex shape: Slightly pointed.
Skin thickness: Average for plum cultivars.
Skin texture: Firm.
Tendency to crack: None known.
Skin:
*Blush color.*—Old Lavender, A-7, Plate 56.
*Flesh color.*—Raw Sienna P+, L-10, Plate 13.
*Flesh color — (Under skin).*—American Beauty, F-6, Plate 6.
*Color — Surface of pit cavity.*—Oak Buff, D-7, Plate 13.
*Color of pitwell.*—Raw Sienna P+, L-10, Plate 13.
Juice production: Slight to moderate.
Flavor:
*Generally.*—Very good, and well balanced.
Aroma:
*Generally.*—Moderate and pleasant.
Texture:
*Generally.*—Firm and solid.
Fibers:
*Numbers.*—Few.
Fibers texture: Relatively tender.
Ripening: Even.
Eating quality: Considered very good.

STONE

Free or cling: Freestone.
Fibers:
*Numbers.*—Few are evident.
Fiber length: Short, approximately 5 mm. (0.2 inches).
Stone size:
*Length.*—Approximately 24–25 mm. (0.94–0.98 inches).
*Width.*—Approximately 16–18 mm. (0.63–0.71 inches).
*Thickness.*—Approximately 12–13 mm. (0.47–0.51 inches).

Form: Oval.
Apex shape: Flat.
Stone sides:
*Surface texture and shape.*—Relatively smooth and slightly uneven.
Ridges: Two raised ridges appear on the ventral side and extend from the base to the apex. These ridges converge on the ventral edge on both sides.
Dorsal edge:
*Surface texture.*—Generally smooth.
Tendency to split: Not evident.
Use: Fresh market.
Keeping and shipping quality: Good as compared to other varieties with which it is most closely similar.
Resistance to disease: Unknown.

Although the new variety of plum tree possess the described characteristics noted above as a result of the growing conditions prevailing near Fresno in the central portion of the San Joaquin Valley of California, it is to be understood that variations of the usual magnitude and characteristics incident to changes in growing conditions, irrigation, fertilization, pruining, pest control, climatic variations and the like are to be expected.

Having thus described and illustrated my new variety of plum tree, what I claim as new and desire to secure by Plant Letters Patent is:

1. A new and distinct variety of plum tree substantially as illustrated and described, and which produces uniformly large, semi-globular fruit, having a very firm flesh with a distinct sweet flavor, the fruit of the present variety being mature for commercial harvesting and shipment approximately the last week of July under the ecological conditions prevailing in the San Joaquin Valley of Central California.

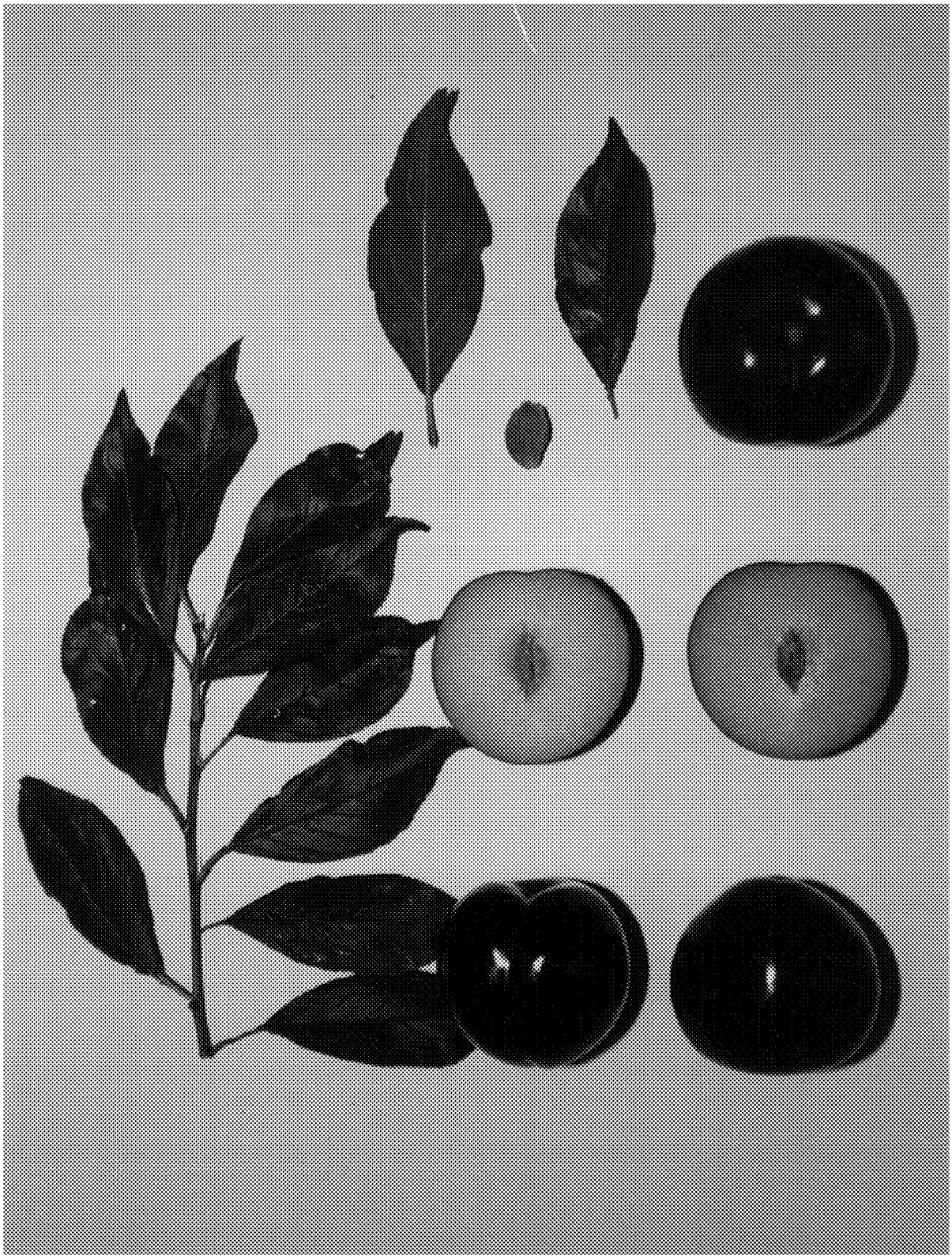

* * * * *